United States Patent
Rannard et al.

(10) Patent No.: US 10,463,618 B2
(45) Date of Patent: Nov. 5, 2019

(54) NANOEMULSIONS

(71) Applicant: The University of Liverpool, Liverpool (GB)

(72) Inventors: Steve Rannard, Liverpool (GB); Andrew Owen, Liverpool (GB); James Hobson, Liverpool (GB); Neill Liptrott, Liverpool (GB); Pierre Chambon, Liverpool (GB)

(73) Assignee: The University of Liverpool, Liverpool (GB)

( * ) Notice: Subject to any disclaimer, the term of this patent is extended or adjusted under 35 U.S.C. 154(b) by 0 days.

(21) Appl. No.: 15/548,702

(22) PCT Filed: Feb. 3, 2016

(86) PCT No.: PCT/GB2016/050252
§ 371 (c)(1),
(2) Date: Aug. 3, 2017

(87) PCT Pub. No.: WO2016/124925
PCT Pub. Date: Aug. 11, 2016

(65) Prior Publication Data
US 2018/0021261 A1   Jan. 25, 2018

(30) Foreign Application Priority Data
Feb. 5, 2015 (GB) .................................. 1501924.3

(51) Int. Cl.
| | |
|---|---|
| *A61K 9/14* | (2006.01) |
| *A61K 9/16* | (2006.01) |
| *A61K 47/10* | (2017.01) |
| *A61K 47/34* | (2017.01) |
| *A61K 9/107* | (2006.01) |
| *C08F 220/28* | (2006.01) |
| *A61K 9/00* | (2006.01) |
| *A61K 31/513* | (2006.01) |
| *A61K 31/536* | (2006.01) |
| *B01F 17/00* | (2006.01) |

(52) U.S. Cl.
CPC .......... *A61K 9/1641* (2013.01); *A61K 9/0053* (2013.01); *A61K 9/107* (2013.01); *A61K 9/1075* (2013.01); *A61K 31/513* (2013.01); *A61K 31/536* (2013.01); *A61K 47/10* (2013.01); *A61K 47/34* (2013.01); *B01F 17/0028* (2013.01); *C08F 220/28* (2013.01); *C08F 2220/286* (2013.01); *C08F 2438/01* (2013.01)

(58) Field of Classification Search
None
See application file for complete search history.

(56) References Cited

U.S. PATENT DOCUMENTS

| | | | |
|---|---|---|---|
| 2011/0195030 A1* | 8/2011 | Mumper | A61K 9/1075 424/9.32 |
| 2015/0218312 A1* | 8/2015 | Wu | C07H 15/04 424/59 |

FOREIGN PATENT DOCUMENTS

| | | |
|---|---|---|
| WO | 2004096422 A1 | 11/2004 |
| WO | 2013024307 A2 | 2/2013 |
| WO | 2014199175 A1 | 12/2014 |
| WO | WO-2014199175 A1 * | 12/2014 ........... C08G 83/004 |
| WO | 2015027342 A1 | 3/2015 |

OTHER PUBLICATIONS

He et al., "Polymer Nanoparticles: Shape-Directed Monomer-to-Particle Synthesis," J. Am. Chem. Soc. (2009); 131 (4):1495-1501.

* cited by examiner

*Primary Examiner* — Susan T Tran
(74) *Attorney, Agent, or Firm* — Fox Rothschild LLP

(57) ABSTRACT

An oil-in-water emulsion comprises an emulsifier which is a non-gelled branched polymer (e.g. a branched vinyl polymer), wherein the ends of at least some of the chains of said polymer terminate in an alkyl chain of 5 carbon atoms or more, and wherein the oil-in-water emulsion takes the form of particles having a z-average diameter of no greater than about 1000 nm. This is useful in, for example, facilitating the carrying of hydrophobic materials within aqueous systems, to enhance oral drug delivery. The oil-in-water emulsion may be prepared by mixing an oil phase with an aqueous phase in the presence of an emulsifier, wherein said emulsifier is a non-gelled branched polymer, wherein the ends of at least some of the chains of said polymer terminate in an alkyl chain of 5 carbon atoms or more, and wherein the oil-in-water emulsion takes the form of particles having a z-average diameter of no greater than about 1000 nm. The oil phase may comprise a further solvent which is miscible with the oil, said solvent being allowed to evaporate to produce the final emulsion.

19 Claims, 13 Drawing Sheets

NANOEMULSIONS

The present invention relates to nanoemulsions and components of, methods of making, and uses of, nanoemulsion compositions. The nanoemulsions are of particular use in oral drug delivery.

Drug delivery is an area of considerable activity and challenge. New methods of delivering known active ingredients can bring considerable benefits, for example in minimising the amount of drug required to treat a particular condition, in ensuring that the drug reaches the desired location, in increasing convenience, in controlling the release profile, and in improving patient compliance. In particular, oral delivery is often desirable, but can be difficult due to the hydrophobic nature of most active ingredients.

Many researchers have looked into ways of dealing with this problem and in particular into ways of dealing with the poor aqueous solubility of drugs.

Encapsulation can be used to isolate and deliver active materials. For example, WO 2013/024307 discloses the use of amphiphilic branched polymer to form oil-in-water emulsions containing active material, followed crosslinking of the polymer to form capsules.

Weaver et al., Angew. Chem. 2009, 121, 2165-2168 discloses assembling large emulsion droplets into larger scale engineered structures.

The present invention is based on research which has identified a particularly effective means of carrying hydrophobic materials within aqueous systems.

From a first aspect the present invention provides an oil-in-water emulsion, comprising an emulsifier which is a non-gelled branched polymer, wherein the ends of at least some of the chains of said polymer terminate in an alkyl chain of 5 carbon atoms or more, and wherein the oil-in-water emulsion takes the form of particles having a z-average diameter of no greater than about 1000 nm.

The emulsions of the present invention are also referred to herein as nanoemulsions because of their small size. They have a mean size wherein at least one dimension, or wherein the z-average diameter (also referred to as the average hydrodynamic diameter), is no greater than about 1000 nm. They may have z-average diameters less than 800 nm, or less than 500 nm, or less than 300 nm, e.g. around 50 to 500 nm, or 200 to 300 nm.

In contrast Weaver et al., Angew. Chem. 2009, 121, 2165-2168 is not concerned with nanoscale structures but rather relates to larger structures. Starting from oil-in-water droplets with an average diameter of 9.2 microns, it aggregates those droplets into larger spheres of the mm scale, and then aggregates those spheres into tubes or other structures of the cm scale. Weaver et al. does not relate to drug delivery applications. The larger scale structures of Weaver et al. are of interest in the fields of inkjet printing and agrochemicals, and other fields where dilution at the point of use is relevant.

The alkyl chains are hydrophobic and therefore associate with the oil phase, and stabilise the oil phase within the aqueous phase.

We have found that effective stabilisation occurs with C5 alkyl or greater, e.g. C6 alkyl (hexyl) or greater, and that in some cases greater stabilisation occurs with C8 alkyl or greater, e.g. C10 alkyl or greater, e.g. C12 alkyl (dodecyl) or greater, e.g. C5 to C20.

The alkyl chains may be branched or unbranched, or a mixture of branched and unbranched.

The alkyl chains may be saturated or unsaturated, or a mixture of saturated or unsaturated.

The alkyl chains may optionally be substituted.

One sub-set of suitable compounds includes those having saturated, unsubstituted, C5-C20 alkyl chains; these are convenient and cost-effective to prepare.

The branched polymer is non-gelled and processable, i.e. exhibits suitable solubility/compatibility to allow dissolution and use as an emulsifier. It can be contrasted with polymer structures which are insoluble and/or exhibit high viscosity, such as extensively crosslinked insoluble polymer networks, high molecular weight linear polymers, or microgels.

The branched polymer may for example be an addition polymer. The branched polymer may for example be a polymer made from unsaturated, e.g. vinyl or allyl, monomers, such as for example acrylate or methacrylate monomers.

Branched vinyl polymers may be prepared by known methods, from monofunctional vinyl monomers and difunctional vinyl monomers (branching agents). They can be made by, but are not limited to being made by, living polymerization, controlled polymerization or conventional chain-growth polymerization techniques such as free radical polymerisation. Several types of living and controlled polymerization are known in the art and suitable for use in the present invention. A preferred type of controlled free radical polymerization is Atom Transfer Radical Polymerization (ATRP); however other techniques such as Reversible Addition-Fragmentation chain-Transfer (RAFT) and Nitroxide Mediated Polymerisation (NMP) or conventional free-radical polymerization controlled by the deliberate addition of chain-transfer agents are also suitable syntheses.

The skilled person is aware of techniques to provide branched but non-gelled vinyl polymers. For example, suitable procedures are described in N. O'Brien, A. McKee, D. C. Sherrington, A. T. Slark and A. Titterton, Polymer 2000, 41, 6027-6031; T. He, D. J. Adams, M. F. Butler, C. T. Yeoh, A. I. Cooper and S. P. Rannard, Angew. Chem. Int. Ed. 2007, 46, 9243-9247; V. Bütün, I. Bannister, N. C. Billingham, D. C. Sherrington and S. P. Armes, Macromolecules 2005, 38, 4977-4982; I. Bannister, N. C. Billingham, S. P. Armes, S. P. Rannard and P. Findlay, Macromolecules 2006, 39, 7483-7492; and R. A. Slater, T. O. McDonald, D. J. Adams, E. R. Draper, J. V. M. Weaver and S. P. Rannard, Soft Matter 2012, 8, 9816-9827. The non-gelled and soluble products of the present invention are different to materials disclosed in L. A. Connal, R. Vestberg, C J. Hawker and G. G. Qiao, Macromolecules 2007, 40, 7855-7863 which are known to comprise multiple cross-linking in a gelled network.

The polymerization of each vinyl polymer chain starts at an initiator. Polymerization of monofunctional vinyl monomers leads to linear polymer chains.

Copolymerization with difunctional vinyl monomers leads to branching between the chains. In order to control branching and prevent gelation there should be less than one effective brancher (difunctional vinyl monomer) per chain. Under certain conditions, this can be achieved by using a molar ratio of brancher to initiator of less than one: this assumes that the monomer (i.e. the monofunctional vinyl monomer) and the brancher (i.e. the difunctional vinyl monomer) have the same reactivity, that there is no intramolecular reaction, that the two functionalities of the brancher have the same or similar reactivity, and that reactivity remains the same even after part-reaction. Of course, the systems and conditions may be different, but the skilled person understands how to control the reaction and determine without undue experimentation how a non-gelled structure may be achieved. For example, under dilute conditions some branchers form intramolecular cycles which limit the number of branchers that branch between chains even if the molar ratio of brancher to initiator (i.e. polymer chain) is higher than 1:1 in the reaction.

Initiators and other reagents used in the polymerisation process are as known in the art. For example, in ATRP, convenient and effective initiators include alkyl halides (e.g. alkyl bromides) and in conventional free radical polymerisation, effective initiators include azo compounds Other suitable types of branched polymers include branched polyesters. These may be prepared by for example ring opening polymerization of monofunctional lactone monomers and difunctional lactone monomers (branching agents). Ring opening polymerization methods and materials are known in the art, for example from Nguyen et al., Polym Chem 2014, 5, 2997-3008.

One sub-set of suitable branched polymers include those comprising ether or polyether moieties, e.g. those comprising polyethylene glycol (PEG) or polyethylene oxide (PEO), e.g. those made from vinyl monomers comprising ether groups. We have found these to be convenient to prepare and to exhibit good properties. Without wishing to be bound by theory, it seems that, whilst the alkyl chains act as anchors in the oil particles, the ether moieties facilitate stabilisation in water. One example of a suitable monomer for use in a method of preparing branched polymers having PEG groups is oligo(ethylene glycol) methacrylate (OEGMA), also known as PEG-methacrylate.

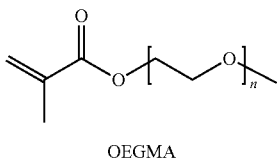

OEGMA

This allows the incorporation of multiple ether moieties on two levels: firstly this monomer already contains several (e.g. 5 to 15) ethylene oxide moieties; and secondly this monomer can be polymerised via its vinyl moiety such that, before connection of the vinyl polymer chains via branches, it may contain for example 30 to 300, e.g. 50 to 200, e.g. 60 to 100, e.g. around 80, OEGMA units (and therefore an order of magnitude more ethylene oxide moieties).

Other suitable monofunctional monomers include, but are not limited to, for example N-butyl methacrylate, hydroxy propyl methacrylate, N,N-diethyl amino ethyl methacrylate, glycerol methacrylate and 2-methacryloyloxyethyl phosphorylcholine. Mixtures of different monomers may be used so as to form a copolymer.

Suitable types of difunctional monomer (i.e. brancher) include for example those which comprise two or more polymerisable functional groups e.g. acrylate or methacrylate monomers.

One example of a suitable brancher is ethylene glycol dimethacrylate (EGDMA). This is convenient and effective.

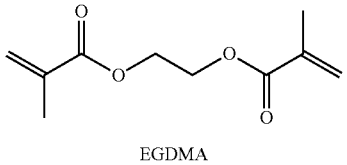

EGDMA

The hydrophobic alkyl chains may be incorporated into the branched polymer via an initiator or chain transfer agent, e.g. via bromide initiators (such as bromo isobutyrates) or mercaptan chain transfer agents. Thus, an initiator (or chain transfer agent) may include an alkyl chain of 5 carbon atoms or more (as defined above). This is a convenient and effective way of imparting the required hydrophobic character so as to stabilise or "anchor" the oil droplets. Furthermore, it is flexible: it enables the alkyl chain ends of the resultant polymer to be varied easily, simply by varying the initiator, and thereby provides an important means of tailoring the composition.

The branched polymer of the present invention can be understood to be a number of linear polymer chains held together with branches between the chains (preferably one branch or fewer per chain) such that some of the chains terminate in hydrophobic alkyl moieties. These hydrophobic "anchors" do not need to be present on each polymer chain. We have surprisingly found that effective emulsification and effective stability can be achieved when 90% or fewer, or 75% or fewer, or 50% or fewer, or even 25% or fewer, of the polymer chain ends carry the required alkyl chain. This means that, where the hydrophobic moieties are incorporated via initiators, only some of the initiators may carry these moieties, and other initiators may have different structures, e.g. may have simpler structures, or may be used to incorporate other chemistry or functionality, e.g. targeting capability or other capability for therapeutic, diagnostic or other biological use.

We have also found that the branched polymers used in the present invention are surprisingly more effective than corresponding linear polymers containing analogous groups, e.g. made from corresponding components except brancher.

Advantageously, the oil-in-water emulsion of the present invention may further comprise a material carried by, or dissolved in, the oil phase. This may be an organic compound, a hydrophobic material, or a material which is soluble in oil or organic solvent. This material may for example be a biologically useful material, e.g. a therapeutically or diagnostically useful material, e.g. a drug or prodrug.

The product of the present invention therefore may preferably be a pharmaceutical composition.

Accordingly, from a further aspect, the present invention provides an oil-in-water emulsion as described above, for use as a medicament.

The present invention also provides a corresponding method of medical treatment comprising administration of an effective amount of an oil-in-water emulsion as defined above, to a subject in need thereof.

The compositions are particularly effective in oral drug delivery. We have found that the emulsions are surprisingly effective in not only maintaining excellent stability but also travelling across model gut systems.

From a further aspect the present invention provides a method of preparing an oil-in-water emulsion comprising mixing an oil phase with an aqueous phase in the presence of an emulsifier, wherein said emulsifier is a non-gelled branched polymer, wherein the ends of at least some of the chains of said polymer terminate in an alkyl chain of 5 carbon atoms or more, and wherein the oil-in-water emulsion takes the form of particles having a z-average diameter of no greater than about 1000 nm.

The features of the emulsifier and of the other components of the emulsion may be as described above.

In an initial step of preparing the nanoemulsions, the drug and/or other pharmaceutical component may be dissolved in an oil. For pharmaceutical uses and therapeutic administration the oil must of course be selected from oils which are suitable for, and safe for, those applications. The skilled person is well aware of oils which fulfil this criterion. Advantageously the oil will be a good solvent for the material to be carried.

Some suitable oils include castor oil, coconut oil, dodecanoic acid, squalene, peanut oil, sesame oil and soy bean oil. Castor oil is particularly preferred with some drugs.

Saturating the oil with the drug will give the maximum possible concentration of the drug in the final emulsion. The nanoemulsion can easily be diluted if required. In contrast it can be difficult to concentrate the emulsion once formed: one method of concentration involves freeze-drying but this can reduce stability and alter the diameter.

We have prepared numerous emulsions with a variety of different drugs. Theoretically the invention is applicable to any lipophilic/hydrophobic drug which has poor aqueous solubility.

Non-limiting examples of some suitable drugs include for example the antiretroviral drugs Lopinavir (LPV) and Efavirenz (EFV), and the antibiotics Rifampicin and Erythromycin. Practically, approximately 50 mg/ml Efavirenz or 25 mg/ml Lopinavir can be dissolved in castor oil.

We have also prepared formulations wherein various other hydrophobic materials are carried, for example Curcumin, Flourescein and Nile Red.

Optionally a further solvent may be used during the preparation procedure in addition to the oil. It is miscible with the oil and also dissolves the drug. The further solvent is not present in the final emulsion and is therefore one which can be removed by evaporation or other methods.

Suitable volatile solvents include for example ethyl acetate, hexane, acetone or THF. Ethyl acetate is one preferred solvent: it is not miscible with water, dissolves the oils, evaporates easily and quickly, and has low toxicity.

The oil (in which the drug etc. is dissolved) is mixed with the volatile solvent. The ratio of oil to solvent can be selected to tailor the size of the nanoemulsion droplets. Typically, the higher the solvent to oil ratio, the smaller the droplets in the final emulsion.

The amount, by volume, of solvent with respect to oil may for example be 50:50 or greater, e.g. 60:40 or greater, e.g. 70:30 or greater, e.g. 80:20 or greater, e.g. 90:10 or greater, e.g. 95:5 or greater, e.g. 99:1 or greater, e.g. 95:5 to 99.9:0.1, e.g. approximately 99:1.

The emulsion is conveniently formed by mixing the oil phase (which optionally includes the volatile solvent) with an aqueous solution of the branched polymer.

The amount of aqueous phase relative to oil phase, and the concentration of the branched polymer within the aqueous phase, can be chosen to tailor the nature and properties of the emulsion. Sufficient polymer should be used to stabilise the nanoemulsion droplets. The concentration of polymer can affect the size of the droplets. Without wishing to be bound by theory, it is believed that lower amounts of polymer lead to larger droplets due to there not being enough polymer to fully encapsulate the droplets and therefore leading to aggregation. Conversely, there is typically an upper limit of polymer required, such that above that amount no further stabilisation benefit will be observed and leading to free polymer in solution.

In some cases, the preferred concentration of polymer in the aqueous phase (w/v) is selected from approximately 0.1-99.9%, 0.5-99%, 1-90%, 1-50%, 1-20%, 2-10%, 3-7%, or approximately 5%.

In some cases, the amount of oil (+solvent) phase relative to the amount of aqueous phase (v/v) is approximately 90:10 to 10:90, or 75:25 to 25:75, or 60:40 to 40:60, or approximately 50:50.

The oil phase and aqueous phase may be mixed and homogenised using any suitable method or apparatus to result in an oil-in-water emulsion. Typically the emulsion will comprise nanosized droplets and will be recognised by a creamy white colour and consistency The volatile solvent may be removed by any suitable method, for example by allowing it to evaporate, and/or by dilution and stirring and/or by passing gas (e.g. inert gas e.g. nitrogen) through the material. We have found that one simple and effective method is simply to leave the material in unsealed containers and allow evaporation (e.g. in a fume cupboard) over a period of 12-48 hours, typically about 24 hours.

Evaporation or removal of the solvent leads to formation of the emulsion in its final form. This has the drug and/or other hydrophobic component(s) present in the oil phase, which oil phase is stabilised in water due to the "coating" of the polymer on the nanodroplets. The z-average diameter, as determined by dynamic light scattering (DLS), is typically 100-500 nm, e.g. 200-300 nm.

The z-average diameters may be measured by DLS at 25° C.

The nanoemulsions are stable on storage and on dilution.

As described below, we have also observed anticoagulant effects of the nanoemulsion formulations and therefore from a further aspect the present invention provides said emulsions, for use as anticoagulants.

The oil-in-water emulsion may have particles or droplets of different sizes to those described above, i.e. not necessarily having a z-average diameter of no greater than about 1000 nm. In other words in a further aspect the present invention provides an oil-in-water emulsion, comprising an emulsifier which is a non-gelled branched polymer, wherein the ends of at least some of the chains of said polymer terminate in an alkyl chain of 5 carbon atoms or more. Other features of such emulsions, and of corresponding compositions, uses and methods, may be as described above.

The present invention will now be described in further non-limiting detail with reference to the following examples and figures in which.

EXAMPLES

Section 1: Preparation of Branched Polymer (Polyoegma DP80 Chains Containing Dodecyl Alkyl Moieties, Linked Using Egdma), and the Use of this to Prepare Nanoemulsions Incorporating Drugs, and Investigations of the Safety and Efficacy of these Nanoemulsions Preparation of Polymer The polymer used to stabilise the nanoemulsions may be made using atom transfer radical polymerisation (ATRP), which is a controlled method of polymerisation, allowing the definition of specific degrees of polymerisation (DP). One example of a water soluble polymer in accordance with the present invention is based on PolyOEGMA DP80.

A DP80 was used, meaning that approximately 80 monomer units (OEGMA) are present per polymer chain. These linear chains are branched together by the use of EGDMA as a branching agent.

Firstly the amount of monomer (OEGMA, Mw 300) was weighed out in a round bottomed flask. The balance was tared, and then the correct amount of EGDMA brancher was added such that there was a 0.95 molar ratio compared to the monomer.

A dodecyl initiator (dodecyl 2-bromoisobutyrate) was then added, followed by a small amount of anisole, which was used as an internal standard for NMR analysis later. Finally, the reaction solvent was added (IPA:$H_2O$; 92.5:7.5). The flask was capped with a rubber scepter and secured in a clamp in the fume hood. Nitrogen gas was pumped into the flask through the scepter in order to remove any oxygen from the flask, through a small gauge needle inserted into the scepter next to the nitrogen inlet needle (oxygen kills the reaction by quenching the radical species).

After 10 minutes of degassing, Copper chloride and BPY were quickly weighed out and combined in a weighing boat, then carefully added to the reaction mixture by slightly removing the scepter to drop in the CuCl/BPY mix. The addition of this started the reaction, and the flask was resealed and allowed to further de-gas for 10 minutes, after which point the outlet needle and nitrogen inlet were removed. Reaction took approximately 8 hours to complete, and this was confirmed by hourly NMR samples to determine the % polymerisation. The molecular weight of the polymer was determined by analysis on gel permeation chromatography.

The exact reaction amounts in this procedure were as follows:

OEGMA 9.44 g
Dodecyl Initiator 0.118 g
EGDMA 62.5 uL
Anisole 400 uL
CuCl 0.034 g
BPY 0.137 g
Solvent 12 mls Preparation of Nanoemulsions Stock solutions of drug dissolved in castor oil were produced (50 mg/ml of Efavirenz in castor oil, or 25 mg/ml of Lopinavir in the same oil).

The drug loaded oil was transferred to a glass vial, and solvent added to achieve a 99:1 solvent to oil ratio. For this ratio, 30 ul of oil was added to the vial, and then mixed with 2970 ul of volatile solvent (ethyl acetate).

Figure 1:
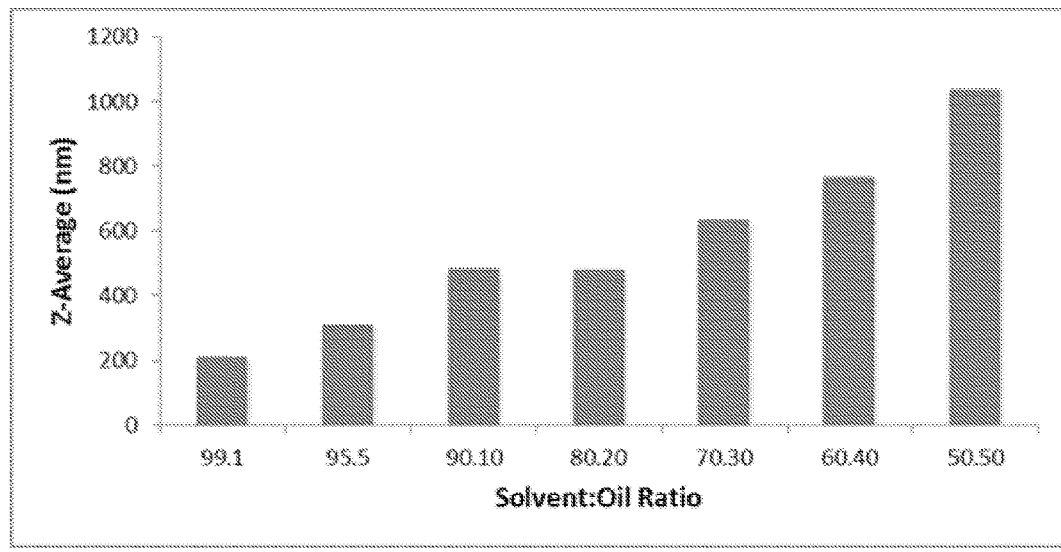
FIG. 1 shows the change in the diameter of a nanoemulsion of the present invention caused by changing the solvent to oil ratio during the preparation process.

Changing the solvent to oil ratio had the effect of changing the diameter of the final nanoemulsion (FIG. 1). FIG. 1 shows z-average values of the final nanoemulsions determined by DLS, based on using the branched polymer with castor oil, ethyl acetate and Efavirenz as described herein.

To 3 ml of oil/solvent, 3 ml of water soluble branched polymer is added, at a concentration of 5% (w/v). The final solution before homogenisation therefore consists of 6 mls.

Figure 2:
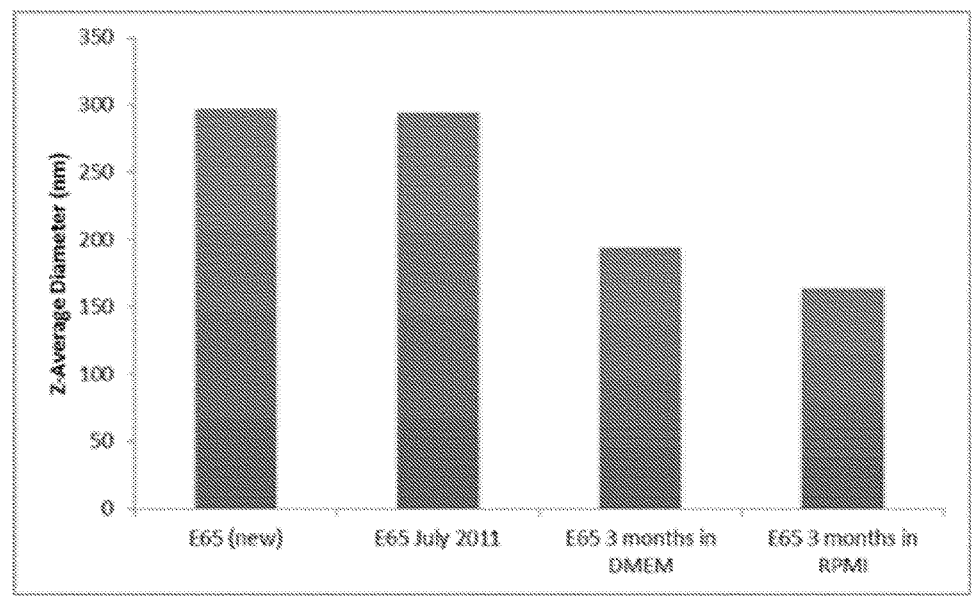
FIG. 2 shows the Z-average diameter of nanoemulsion samples on storage.

The concentration of 5% (w/v) is used as it fully stabilises the nanoemulsion droplets, giving them the smallest diameter, and allowing for stability at that diameter for greater than 2 years post homogenisation (FIG. 2). In FIG. 2, "E65 July 2011" was a sample made in July 2011, stored and then resized in July 2013. Excellent stability over time is observed. DMEM and RMPI are cell culture media, into which E65 was dispersed and then stored in the fridge and resized 3 months later. (E65 was a sample based on using the branched polymer with castor oil, ethyl acetate and Efavirenz as described herein).

Figure 3:
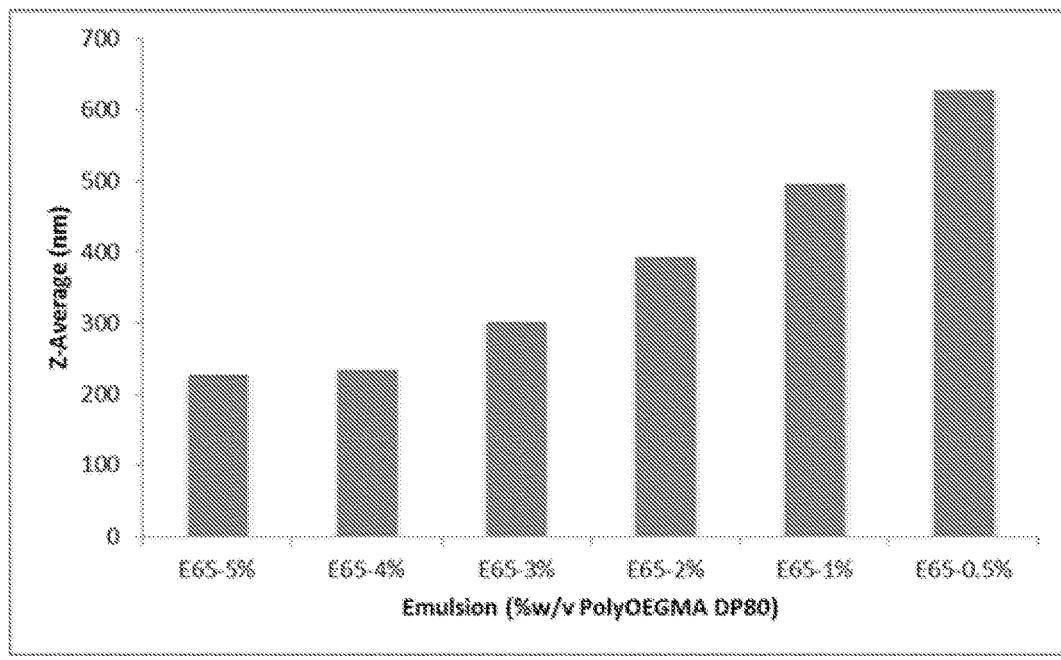
FIG. 3 shows the effect of amount of polymer on nanoemulsion diameter.

Changing the concentration of the polymer increases the diameter of the droplets, even when the solvent to oil ratio remains constant. This is suggestive of there not being enough polymer present in the lower concentrations to fully encapsulate the oil droplets, leading to them aggregating (FIG. 3). FIG. 3 shows the z-average diameter in respect of the final emulsion as a function of the concentration of branched polymer in the aqueous phase. At concentrations above 5% (w/v) there was no further reduction in diameter observed, and thus using concentrations above this value would only lead to residual free polymer in the nanoemulsion.

The two-phase solution was homogenised for 2 minutes using a Ultra Thuraxx T-25 digital homogeniser fitted with a S 25 N-10G dispersing element, and set to maximum speed of 25,000 RPM. During the 2 minutes, the vial was rotated clockwise for 30 seconds, anticlockwise for 30 seconds, and then up and down for 1 minute.

Any suitable homogeniser could be used, provided it is capable of the forces necessary to adequately mix the solution and "chop" up the oil into the nanosized droplets. The process of rotating the vial could be altered, but in the present experiments was kept the same in order to achieve continuity between batches of nanoemulsions.

After homogenisation the samples could be seen to be emulsified by their now creamy white colour and consistency.

The vials were left in the fume hood without capping for 24 hours, which allows the volatile solvent to evaporate at ambient temperature and collapse the oil droplets, resulting in formation of highly stable oil in water emulsions. Other methods for removing the volatile solvent have included diluting into water and stirring, and diluting into water and passing nitrogen through the samples. The diameters of the droplets produced in these methods was identical to simply leaving the vial open overnight.

The drug was present in the oil phase, stabilised by a coating of the polymer, and having a Z-average diameter of around 200-300 nm as determined by DLS (FIG. 2). The final volume of the sample prepared in this exact method was 3 mls.

Figure 4:
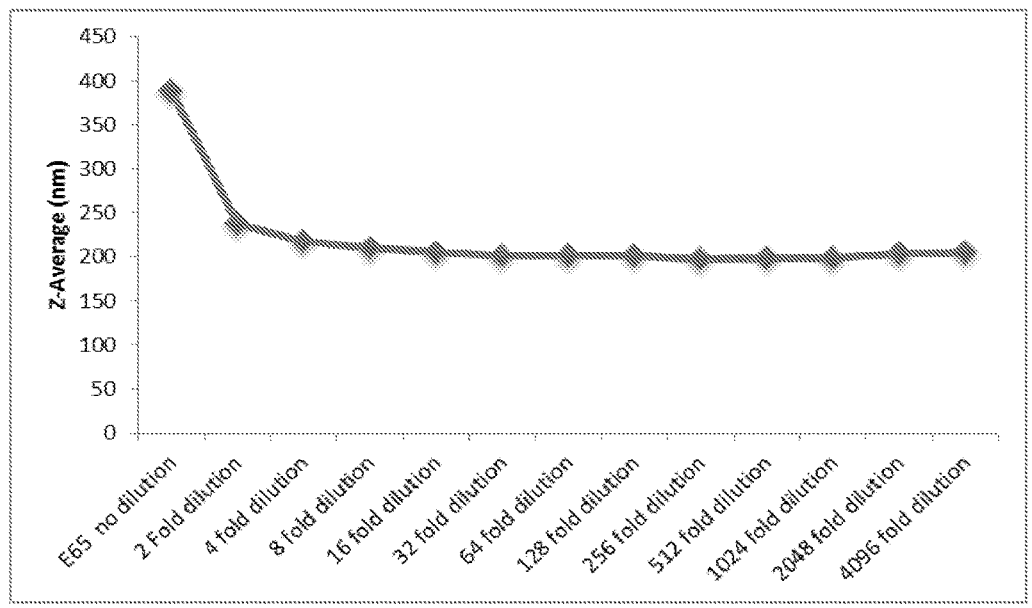
FIG. 4 shows the Z-average diameters of nanoemulsion after serial dilution.

The final nanoemulsion also remained stable when diluted in order to obtain the appropriate concentrations for various cellular analysis. This was confirmed by diluting the nanoemulsion until it could no longer be seen by the DLS (FIG. 4).

Nanoemulsion Safety

Immunological assessment was performed using three separate assay procedures. For all experiments, peripheral blood mononuclear cells were used, extracted from whole blood using a Ficoll centrifugation gradient method.

Initially, the expression of cell surface activation markers (CD25, CD44, CD69 and CD95) were determined using both CD4+ and CD8+ cells separated from the PBMC's by magnetic separation using the MACS system (Miltenyi Biotech). The data showed that there was no increase in the expression of the activation markers as a result of exposure to the nanoemulsion formulation, indicative of a non-immunogenic compound, at least in vitro. Indeed, the nanoemulsion was comparable to a standard aqueous solution in terms of its impact upon expression of cell surface markers (FIG. 5).

Figure 5:
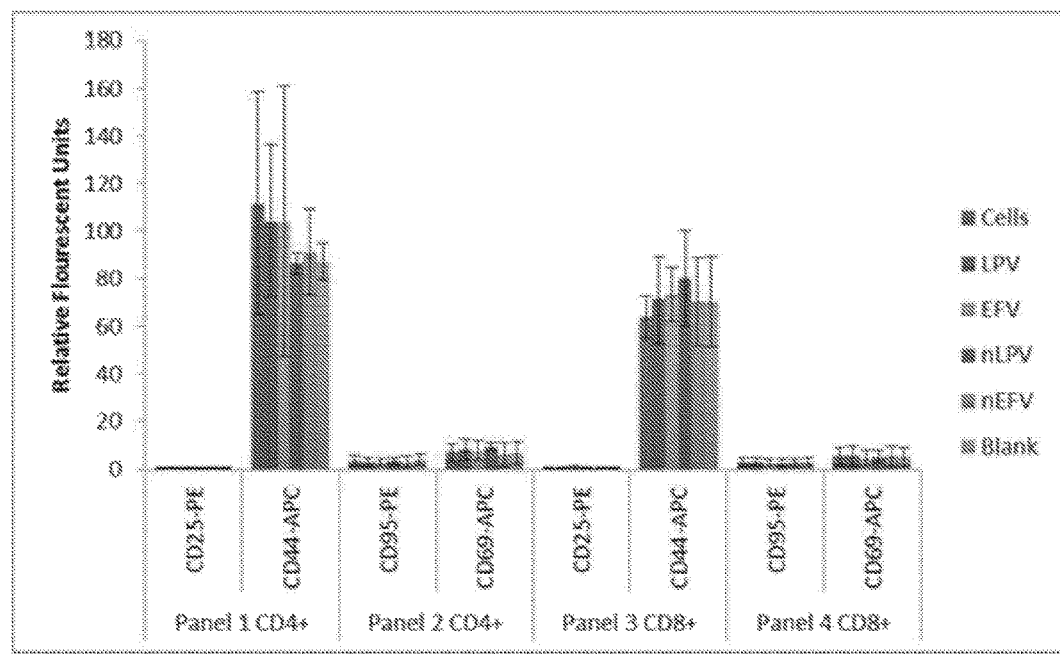
FIGS. 5 to 7 show immunological results in respect of nanoemulsions of the present invention in comparison to controls.

FIG. 5 shows expression levels of cell surface activation markers after 24 hour exposure to aqueous or nanoemulsion (n) formulations of Lopinavir (LPV) and Efavirenz (EFV). The nanoemulsion was, prepared as described above, using 99:1 ethyl acetate:castor oil, with branched polymer as described above (polyOEGMA with C12 alkyl moieties and branched using EGDMA), and including LPV or EFV ("nLPV" or "nEFV"—the "n" denotes nanoemulsions) or no drug at all ("blank"). The legend, from top to bottom, corresponds to the bars from left to right in each case.

Figure 6:
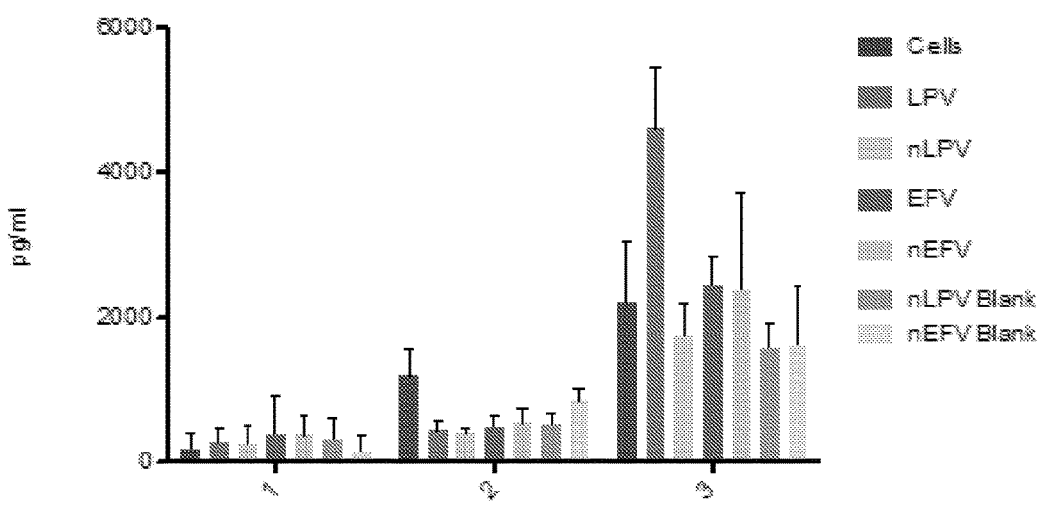

The extracellular media of the expression assay was isolated and analysed for the secretion levels of cytokines IL-2, IL-10 and IFN gamma using a Bioplex 200 system and assay kit (Bio-Rad). Data for cells that were pre-stimulated with a T-cell activation kit (Miltenyi Biotech) showed that the levels of cytokines secreted by those cells exposed to nanoemulsions similar to those observed after exposure to aqueous solutions of the same drugs. In the case of IFN gamma, the LPV nanoemulsion was more comparable to the control with respect to its secretion profile, than was the aqueous solution of LPV (FIG. 6). FIG. 6 shows secretion levels of cytokines IL-2 (1), IL-10 (2) and IFNg (3) after 24 hour incubation with aqueous or nanoemulsion ARV formulations. The same experiment was conducted on un-stimulated cells, with the results showing undetectable levels of cytokines across all conditions (data not shown).

Figure 7:
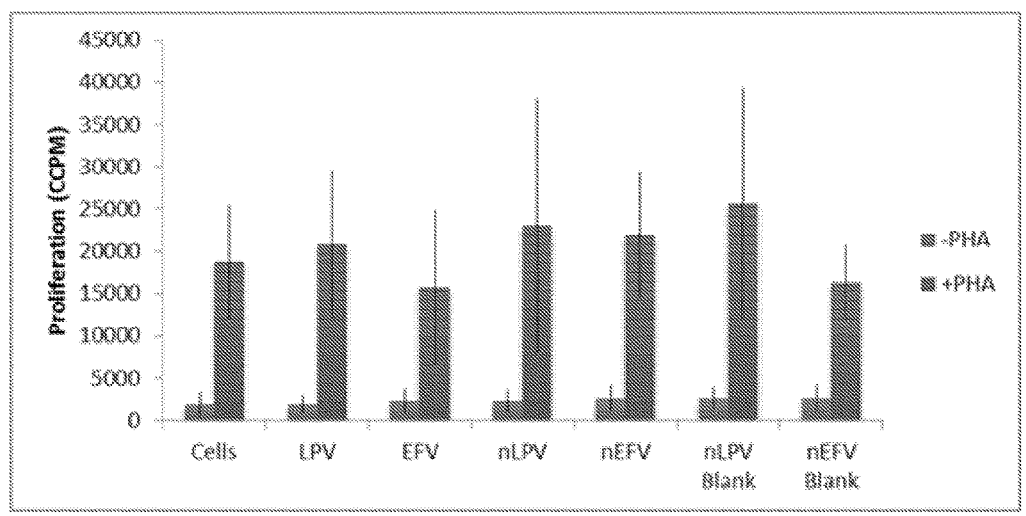

The effect of the nanoemulsion on the cellular proliferation of PBMCs was also investigated, using a $^3$H-Thymidine incorporation assay. Briefly, PBMCs were grown for 72 hours in the presence of aqueous solution or nanoemulsion equivalent, with $^3$H-Thymidine added during the last 16 hours of incubation. Radiometric analysis was used to determine any effect of these incubations on proliferation. The experiment was conducted with and without the addition of Phytohaemagglutinin (PHA), used to stimulate the cells to proliferate. The data showed that across all formulations and conditions, no differences were observed between treated and untreated cells (FIG. 7).

Anticoagulant Efficacy

The impact of nanoemulsion formulations on plasma coagulation was also assessed. Human blood from three donors was collected by venepuncture into tubes anti-coagulated with sodium citrate; blood was used within one hour of collection. Test plasma was prepared by centrifuging blood at 2500×g, at 21° C., for 10 minutes with the resultant plasma collected and pooled. Pooled plasma was stable at room temperature for 8 hours. Nanoemulsion samples were prepared at 10× the required final concentration to accommodate dilution when added to test plasma. Concentrations and subsequent dilutions were based on the concentration of Efavirenz contained within the samples with dilutions of blank nanoemulsion diluted in the same fashion. Final concentrations tested were 40 µg/mL, 4 µg/mL, 0.8 µg/mL and 0.16 µg/mL. Nanoemulsion samples were mixed with test plasma and incubated at 37° C. for 30 minutes. Each nanoemulsion preparation was prepared in triplicate. Lyophilised controls representing normal and abnormal plasma (plasma with coagulation delay) were reconstituted with distilled water (2 mL) and left to equilibrate to room temperature 30 minutes prior to use.

Assays are designed to capture interactions of nanoemulsions with components of the three major coagulation pathways; intrinsic pathway (also known as the contact activation pathway, because it is activated by a damaged surface), extrinsic pathway (also known as the tissue factor pathway) and the final common pathway. Activated partial thromboplastin time (APTT) assay is used to assess the intrinsic pathway while the prothrombin time (PT) assay is a measure of the extrinsic pathway. Thrombin time (TT) is an indicator of the functionality of the final common pathway.

Cuvettes were placed into A, B, C and D test rows on the coagulometer and one metal ball added into each cuvette (warmed for at least 3 minutes prior to use). 100 µL of either control or test plasma was added to a cuvette when testing PT or thrombine time and 50 µL when testing APTT with three duplicate cuvettes for each plasma sample. Additionally, for the APTT assays 50 µL of PTT-A was also added. Timer was started for each of the test rows and cuvettes transferred to PIP row 10 seconds prior to alarm notification. Once incubation time was complete coagulation reagent was added to each cuvette and coagulation time recorded. Percentage coefficient of variation was calculated for each control and test samples according to the following formula: % CV=SD/Mean×100%. If % CV was greater than 5% for study samples that sample was reanalyzed. Data was expressed as a percentage of the coagulation time recorded for plasma with no nanomaterial present (plasma only control).

Figure 8A:
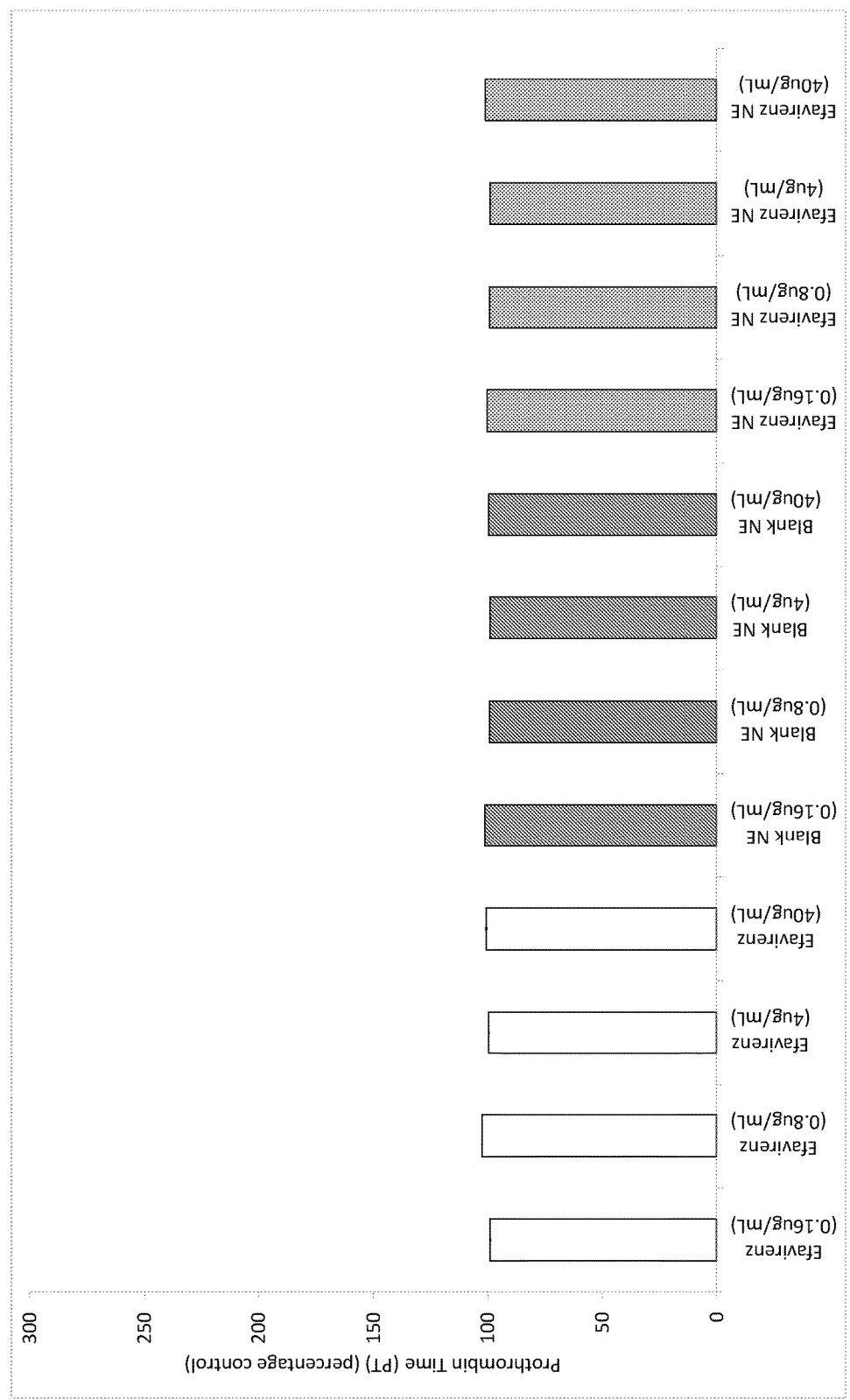
FIG. 8 shows the impact of nanoemulsions on plasma coagulation—healthy volunteer plasma was treated with Efavirenz, blank nanoemulsion and Efavirenz containing nanoemulsion prior to analysis of prothrombin time (a), thrombin time (b) and activated partial thromboplastin time (c)
Figure 8B:
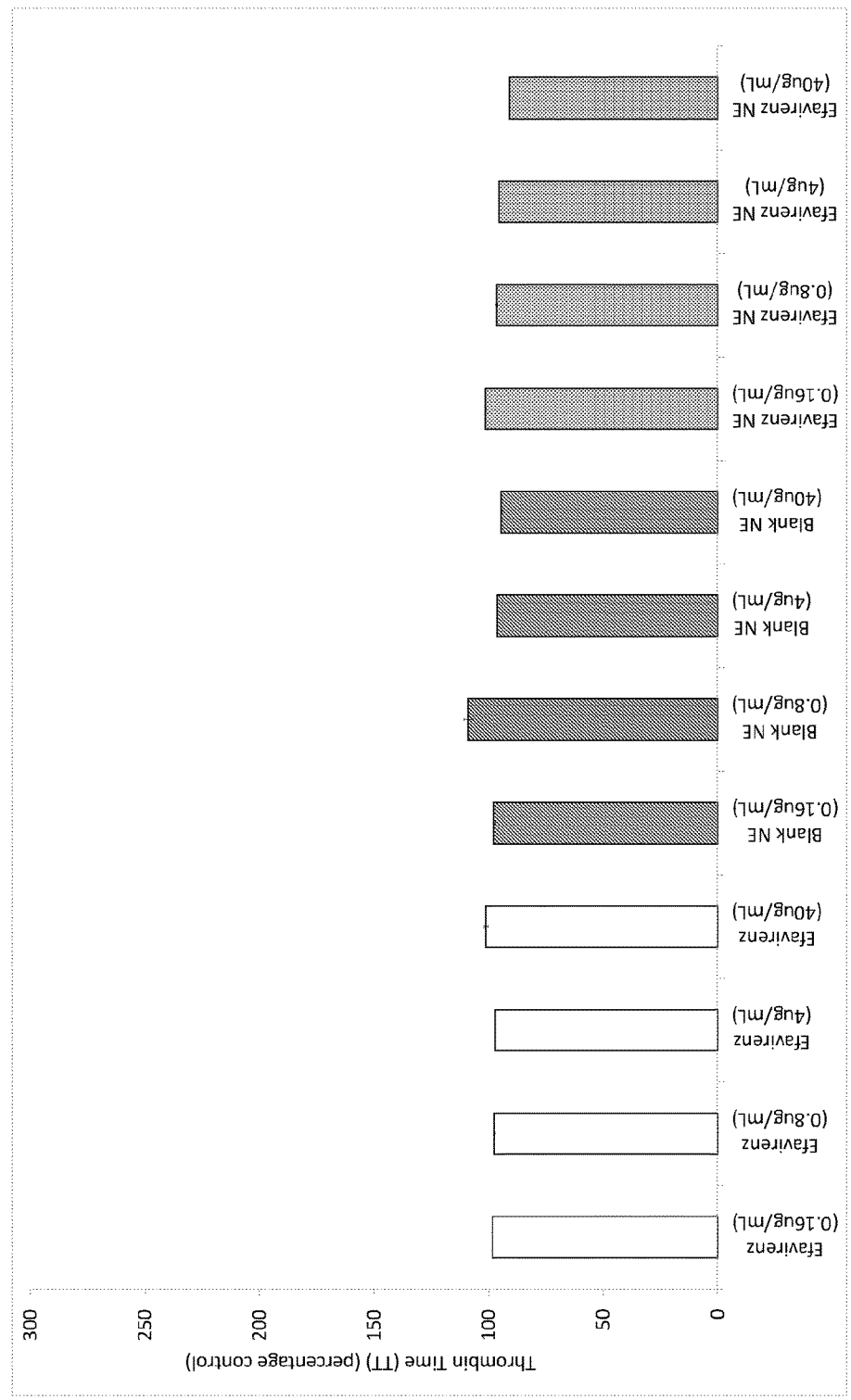
Figure 8C:
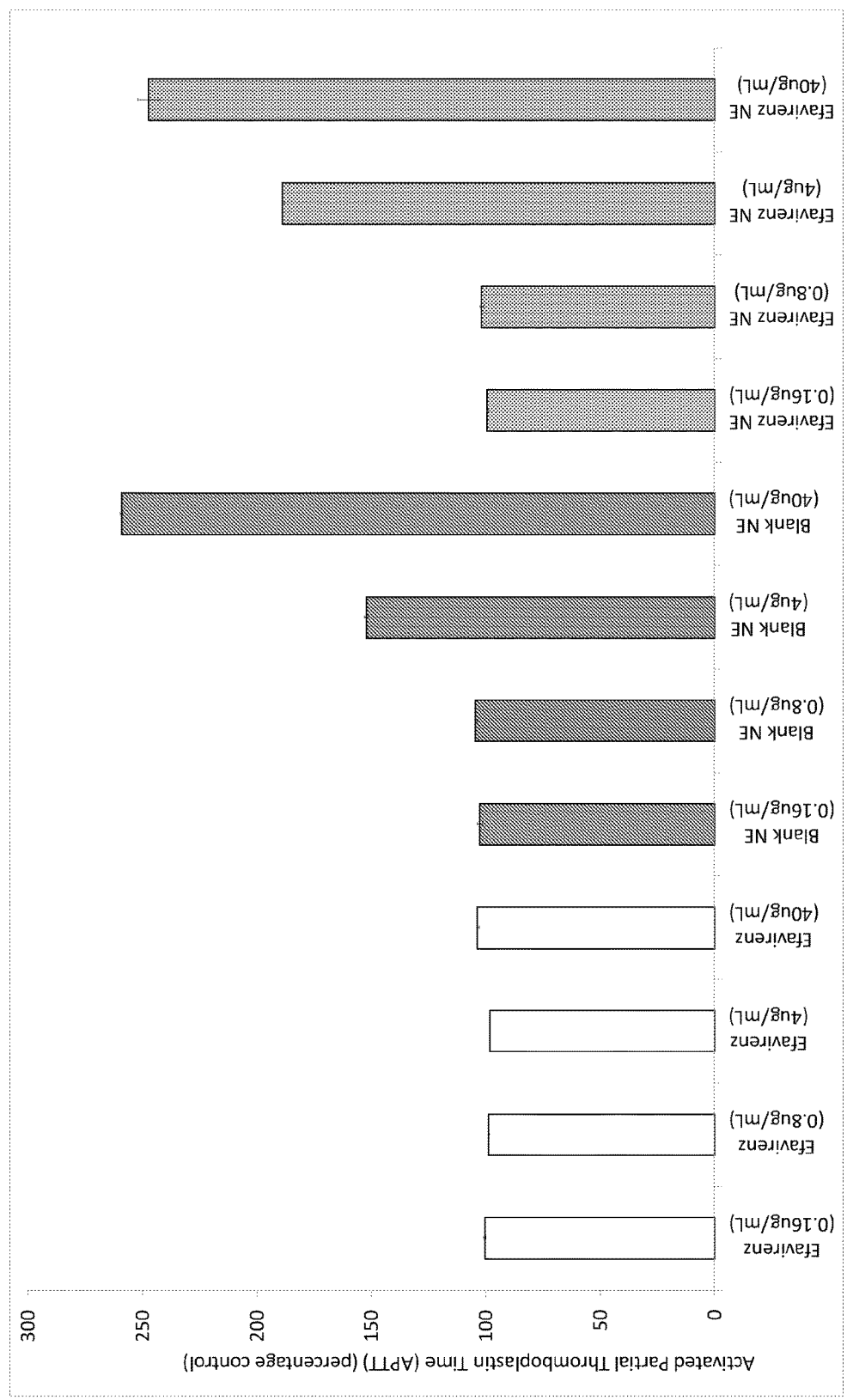

No impact on either PT (FIG. 8a) or TT (FIG. 8b) by Efavirenz solution, blank nanoemulsion or nanoemulsion containing Efavirenz was observed. Marked prolongation of coagulation time in the APTT assay (FIG. 8c) was observed for the blank nanoemulsion at 40 µg/mL (159% greater coagulation time) and 4 µg/mL (52% greater coagulation time). A similar impact on prolongation times for the Efavirenz containing nanoemulsions at 40 µg/mL (147% greater coagulation time) and 4 µg/mL (88% greater prolongation time). However Efavirenz solution did not impact on coagulation time at all suggesting that prolongation of APTT was influenced by nanoemulsions, or constituent material, themselves.

Here we have demonstrated the anticoagulant properties for a novel nanoemulsion. Additionally this nanoemulsion has been demonstrated to prolong coagulation time via one specific coagulation pathway thereby potentially mitigating unwanted side effects.

Efficacy with Antiviral Drugs

The antiviral activity of the nanoemulsion formulations was assessed against the laboratory-adapted strain HIV-1 IIIB, using an MTT assay to determine the viability of a human lymphocyte CD4+ cell line (MT4), after exposure to the virus (with and without aqueous or nanoemulsions). Cells were incubated for a period of 5 days. The data showed that the antiviral activity for the nanoemulsion formulations was similar to that of aqueous solutions, with $IC_{50}$ values of 0.46 μM and 0.18 μM for LPV and EFV, respectively.

Figure 9:
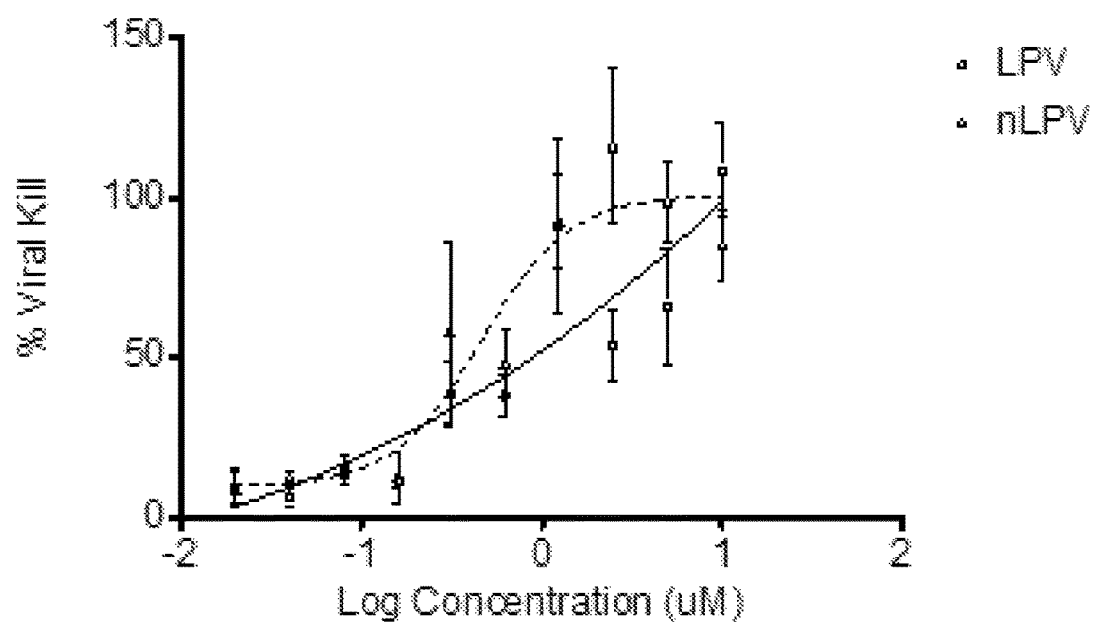
FIG. 9 shows the efficacy of nanoemulsion-drug formulations of the present invention in comparison to control drug formulations.
Figure 9:
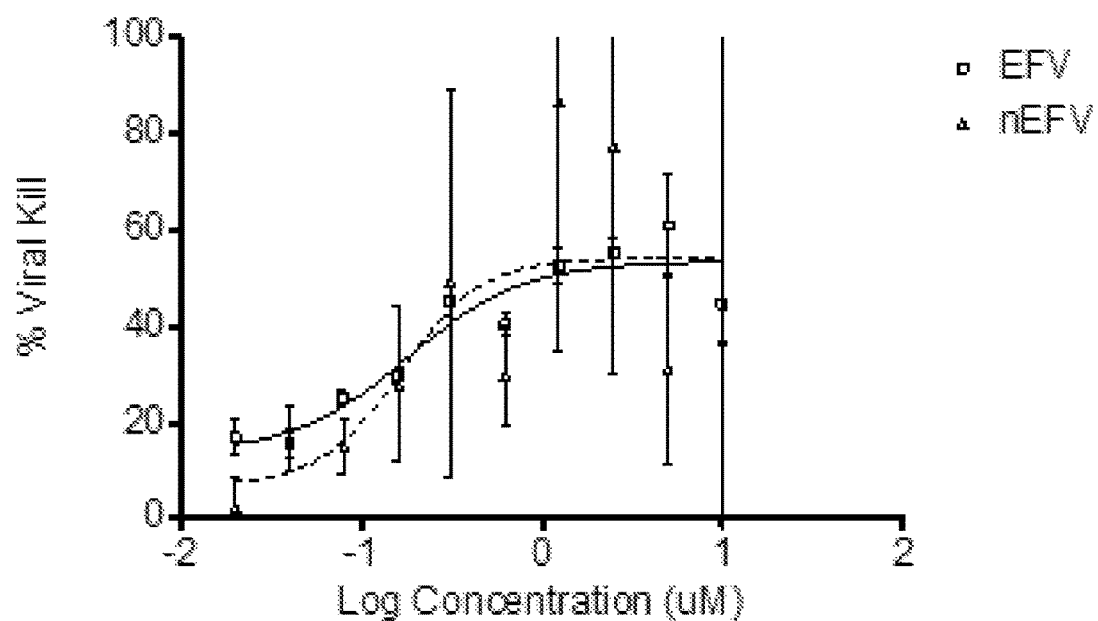

FIG. 9 shows viral kill curves of HIV-1 IIIB based upon viability of MT4 cells incubated with either Aqueous or nanoemulsion formulations of LPV (top) and EFV (bottom).

The dose response curve for nanoemulsion EFV was identical to that of aqueous EFV, whereas nanoemulsion LPV had a greater viral kill at lower concentrations, as compared with aqueous solution.

with primary alcohols. These initiators included the following, in decreasing order of hydrophobicity:

Dodecyl bromoisobutyrate (DBIB), a C12 initiator
Hexyl bromoisobutyrate (HBIB), a C6 initiator
Ethyl isobutyrate (EBIB), a C2 initiator
$PEG_{750}$ bromoisobutyrate (PBIB), a polyethylene oxide macroinitiator These initiators were prepared in accordance with reactions as summarized in the reaction schemes below (EBIB was also purchased from Sigma Aldrich). Reagents were purchased from Sigma Aldrich. The PEG initiator was synthesized from monomethoxy PEG with an average molecular weight of 750 g mol-1.

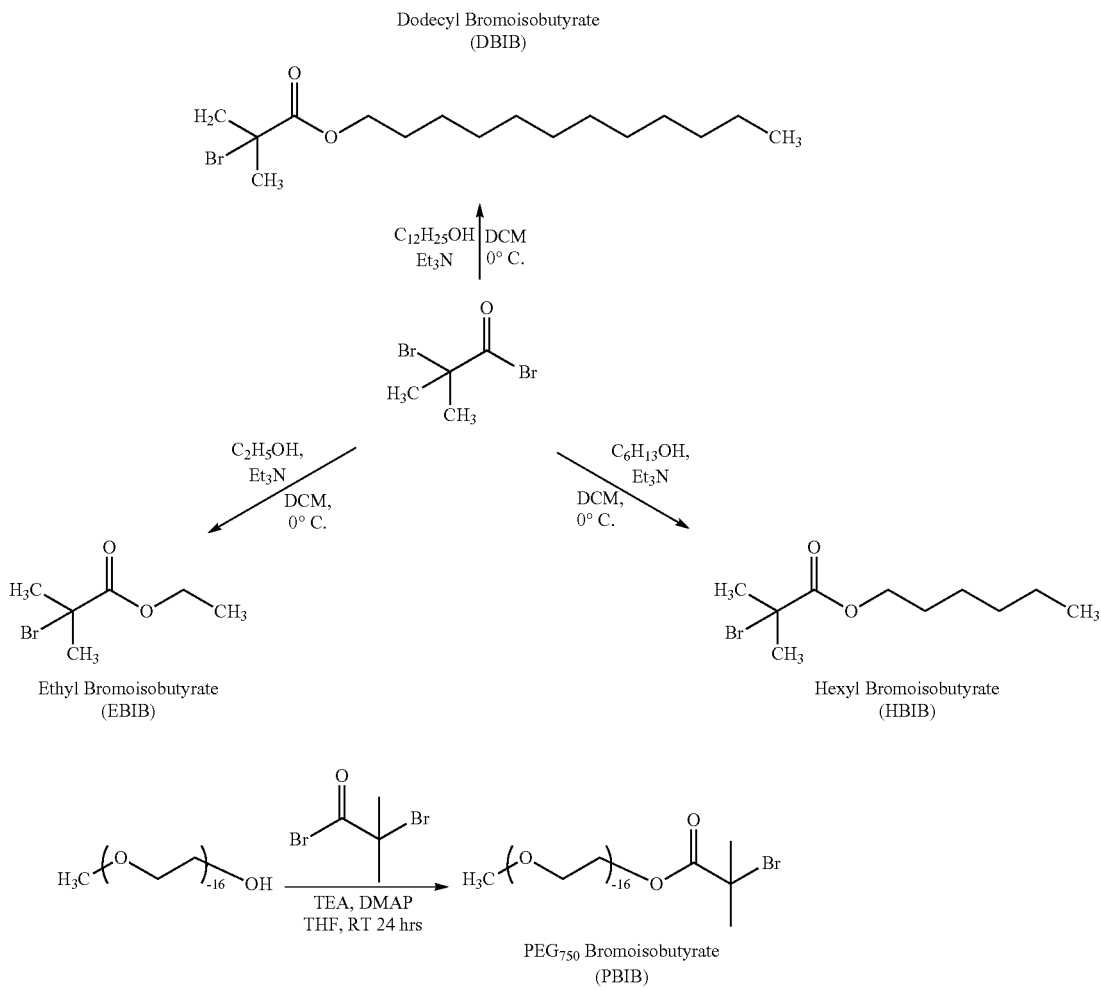

Thus, the present invention provides compositions which not only exhibit good stability, but which also do not display cytotoxicity or immune response issues, and furthermore are efficaceous.

Section 2: Further Investigations of the Effects of Varying the Type and Amount of Hydrophobic Group, including the Use of Mixed Initiators, and of the Properties of Branched Polymers Compared to Analogous Linear Polymers Initiators Several ATRP initiators with varied hydrophobicity were prepared by esterification of alpha-bromoisobutyryl bromide Preparation of Polymers The initiators were used in the polymerization of OEGMA to give linear polymers and in the preparation of OEGMA and EGDMA to give statistical branched polymers. A branching agent (EGDMA) to initiator ratio of 0.80:1 was used to avoid gelation.

Polymerizations were carried out using single initiators so as to result in homo-functionalised end groups, and also using mixed initiators to produce statistical polymers with mixed end group functionality.

Polymerisations were carried out with a target degree of polymerization (DP) of 80 units of monomer OEGMA per linear chain; the resultant linear polymer is denoted pOEGMA$_{80}$. This was done with each initiator; in each case polymerization achieved 85-90% conversion to result in linear polymers with similar weight properties (according to GPC), as shown in the following table.

| Linear Polymer System | Initiator | Mw (kg mol$^{-1}$) | Mn (kg mol$^{-1}$) | Đ |
|---|---|---|---|---|
| pOEGMA80 | DBIB (100%) | 45.6 | 29.55 | 1.5 |
| pOEGMA80 | HBIB (100%) | 42.8 | 28.8 | 1.5 |
| pOEGMA80 | EBIB (100%) | 46.0 | 30.9 | 1.5 |
| pOEGMA80 | PBIB (100%) | 43.5 | 29.2 | 1.5 |

Branched analogues were prepared by polymerization in the presence of EGDMA. Polymerisations were optimized to result in monomer conversions of over 99%, and again similar molecular weight properties were observed across the range of initiators, as shown in the following table.

| Branched Polymer System | Initiator | Mw (kg mol$^{-1}$) | Mn (kg mol$^{-1}$) | Đ |
|---|---|---|---|---|
| pOEGMA80-EGDMA0.8 | DBIB (100%) | 535 | 65.9 | 8.1 |
| pOEGMA80-EGDMA0.8 | HBIB (100%) | 384 | 63.5 | 6.0 |
| pOEGMA80-EGDMA0.8 | EBIB (100%) | 487 | 70.6 | 6.9 |
| pOEGMA80-EGDMA0.8 | PBIB (100%) | 496 | 56.9 | 8.7 |

Thus, hydrophobicity can be tailored without significantly altering other properties of the polymers, by changing the initiator.

Further branched analogues were prepared using mixed initiators. A variety of systems were tested. By way of example, one representative system used DBIB and EBIB in varying ratios. Again, the reactions proceeded with over 99% monomer conversion and produced polymers of similar molecular weight characteristics, as indicated in the table below. Thus, the present invention allows fine tuning of the hydrophobicity, and also allows flexibility in that initiators may be varied for other reasons.

| Polymer | DBIB (mol %) | EBIB (mol %) | Mw (kg mol-1) | Mn (kg mol-1) | Đ |
|---|---|---|---|---|---|
| pOEGMA80-EGDMA0.8 | 100.0 | 0.0 | 535 | 65.9 | 8.1 |
| pOEGMA80-EGDMA0.8 | 74.3 | 25.7 | 497 | 63.1 | 7.9 |
| pOEGMA80-EGDMA0.8 | 50.1 | 49.9 | 537 | 76.1 | 7.1 |
| pOEGMA80-EGDMA0.8 | 25.5 | 74.5 | 307 | 58.6 | 5.2 |
| pOEGMA80-EGDMA0.8 | 9.2 | 90.8 | 511 | 68.4 | 7.5 |
| pOEGMA80-EGDMA0.8 | 0.0 | 100.0 | 487 | 70.6 | 6.9 |

Use of the Polymers as Emulsifiers

In model systems, emulsions were prepared using 1:1 by volume of dodecane oil and aqueous polymer solution. Emulsions were homogenized using a high shear mixer for two minutes. In the absence of polymeric emulsifier phase separation resulted within 5 minutes.

Comparison of Emulsions Prepared from Linear and Branched Polymers

DBIB, HBIB and EBIB were each used individually in the polymerisation of linear pOEGMA$_{80}$, and in the polymerization of branched pOEGMA$_{80}$-EGDMA$_{0.8}$. These were then used to prepare emulsions. The mean droplet size and distribution of the emulsions were studies over a 29 day time period.

Figure 10:
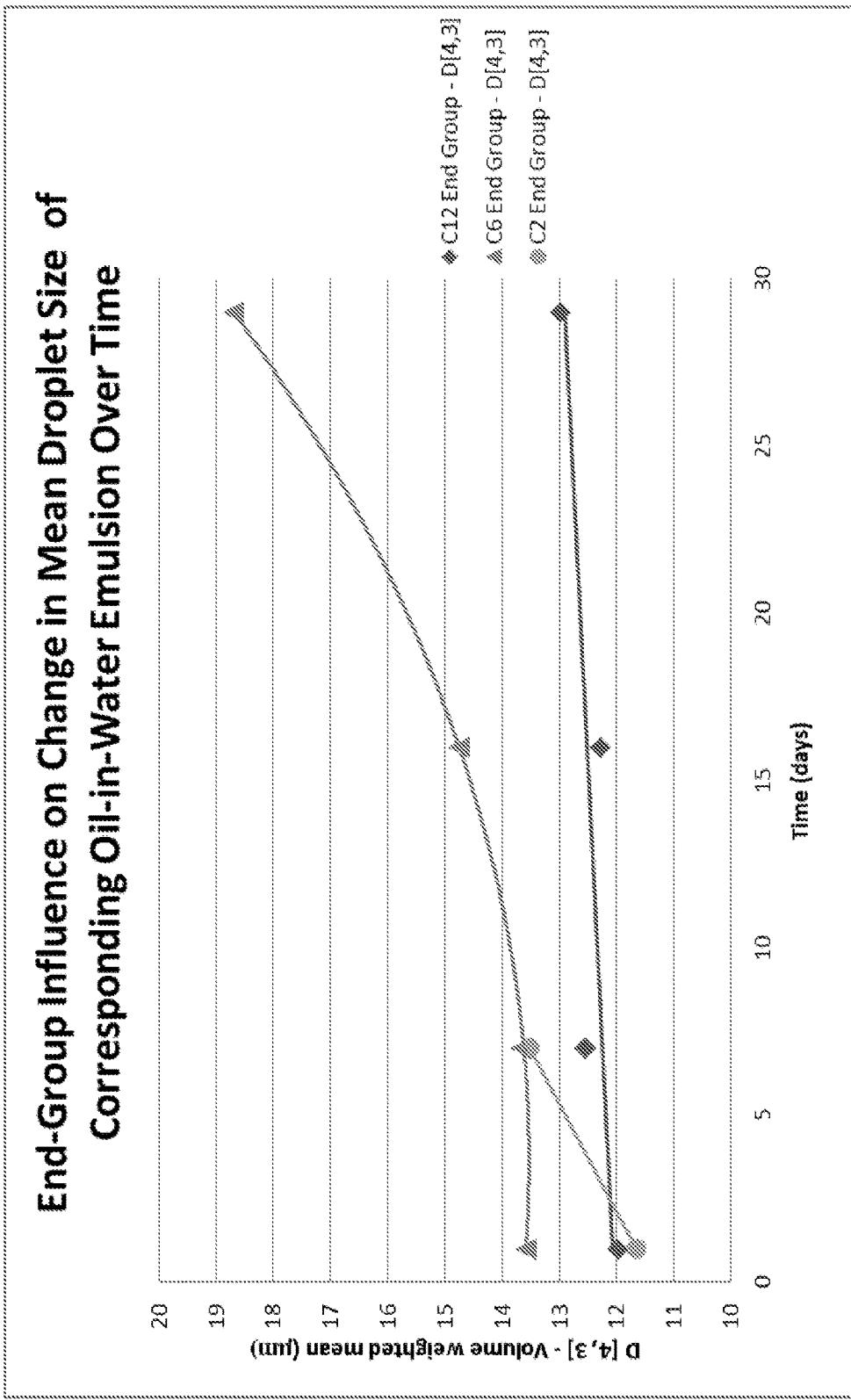
FIGS. 10 and 11 show the stability provided by branched polymer emulsifiers in accordance with the present invention compared to corresponding linear polymer emulsifiers (comparative example)
Figure 11:
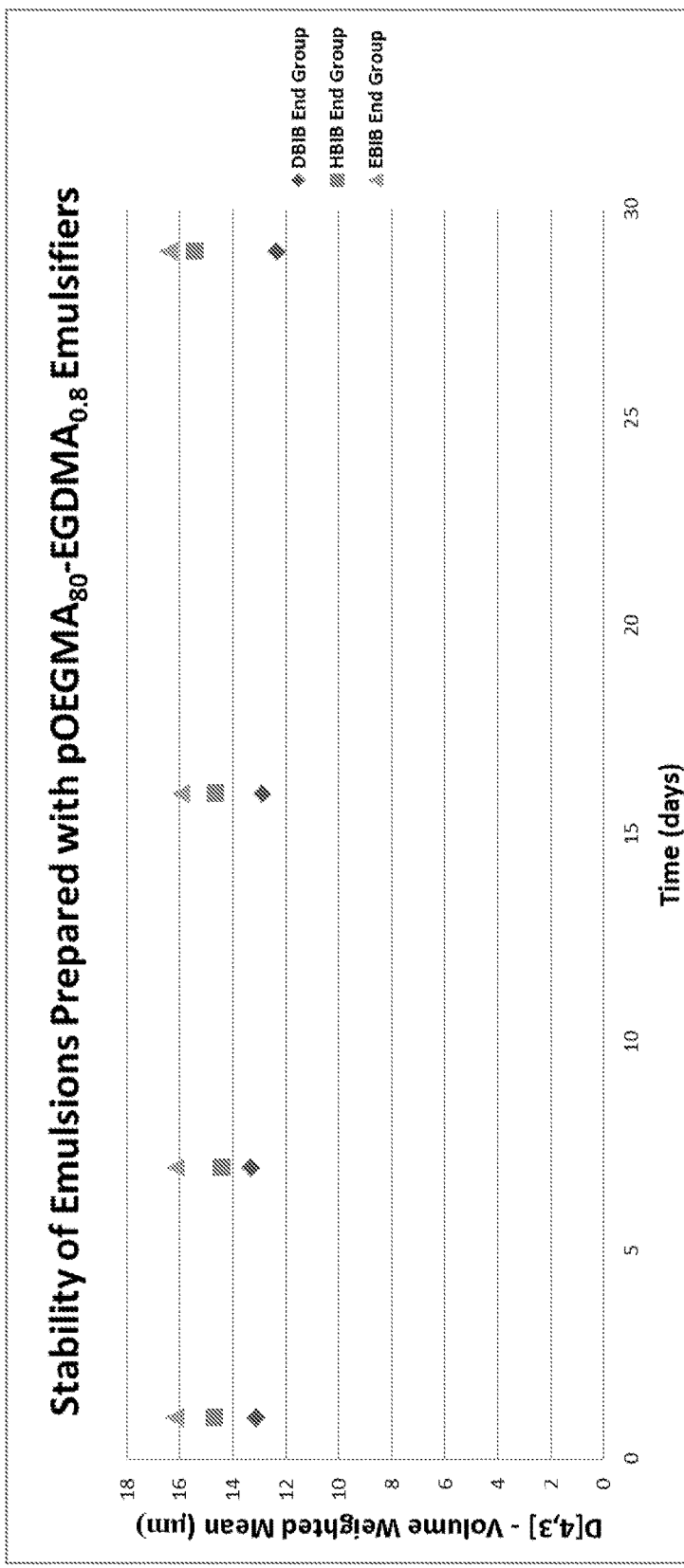

The linear polymers produced emulsions which has similar droplet sizes to start with, but then the mean droplet size increased by different extents depending on the initiator which had been used (EBIB resulting in the least stable emulsions, followed by HBIB, followed by PBIB). In contrast, all of the branched polymers remained stable over the entire time period; no coalescence was observed and no significant change was seen in mean droplet size over time, which was similar for all branched polymers. The differences can be seen in FIG. 11 (showing the mean droplet size, as a function of time, of emulsions prepared using the branched polymers) compared to FIG. 10 (showing the mean droplet size, as a function of time, of emulsions prepared using the corresponding linear polymers).

Without wishing to be bound by theory, the branched architecture seems to provide an increased anchoring ability due to a multiple end group effect, multiple anchors being assembled on the same structure.

Emulsions Prepared from Branched Polymers having Mixed Initiators

Several branched pOEGMA$_{80}$-EGDMA$_{0.8}$ polymers were prepared using mixed initiator systems, and used to prepare emulsions. One non-limiting set of examples used DBIB and EBIB in varying ratios as shown in the following table.

| Polymer | Polymer Conc./mg ml$^{-1}$ | Dodecane (mls) | Water (mls) | DBIB (%) | EBIB (%) | D[3,2] (μm) | D[4,3] (μm) |
|---|---|---|---|---|---|---|---|
| pOEGMA80 - EGDMA0.8 | 5.00 | 3.00 | 3.00 | 100 | 0 | 11.82 | 13.11 |
| pOEGMA80 - EGDMA0.8 | 5.00 | 3.00 | 3.00 | 75 | 25 | 11.86 | 13.01 |
| pOEGMA80 - EGDMA0.8 | 5.00 | 3.00 | 3.00 | 50 | 50 | 11.90 | 13.18 |
| pOEGMA80 - EGDMA0.8 | 5.00 | 3.00 | 3.00 | 25 | 75 | 12.34 | 13.68 |
| pOEGMA80 - EGDMA0.8 | 5.00 | 3.00 | 3.00 | 10 | 90 | 13.92 | 15.43 |
| pOEGMA80 - EGDMA0.8 | 5.00 | 3.00 | 3.00 | 0 | 100 | 14.29 | 16.17 |

Figure 12:
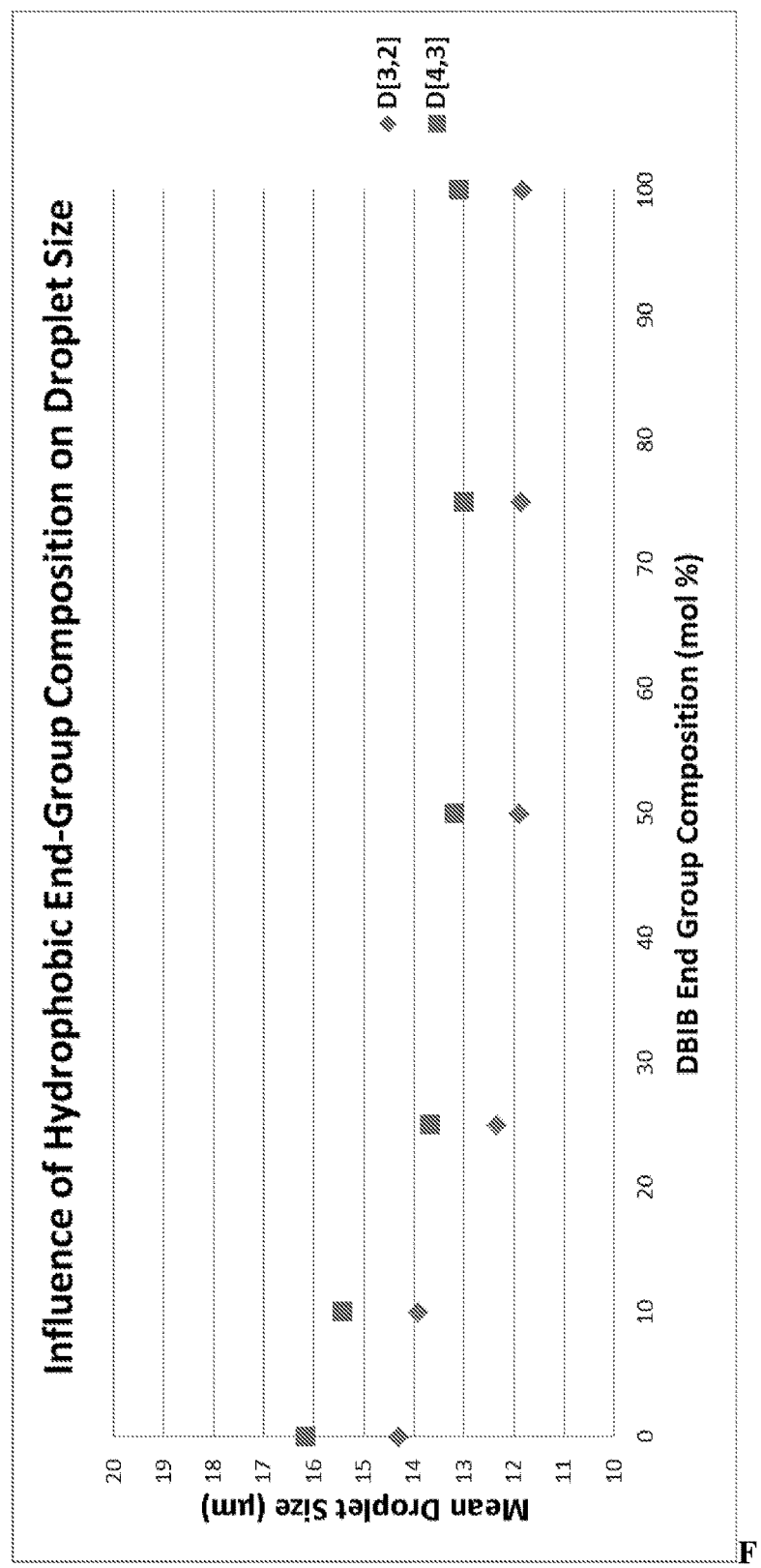
FIG. 12 shows how mean droplet sizes of certain emulsions prepared with mixed initiators in accordance with the present invention vary as a function of amount of hydrophobic initiator compared to other initiator.

EBIB is relatively hydrophilic compared to hydrophobic DBIB. DBIB provides a good anchoring effect, even when some EBIB is present. In fact, it can be seen that even as little as 25 mol % of DBIB is sufficient to produce stable emulsions before any significant change in mean droplet size, as illustrated in FIG. 12.

Transcellular Permeation Experiments

Figure 13A:
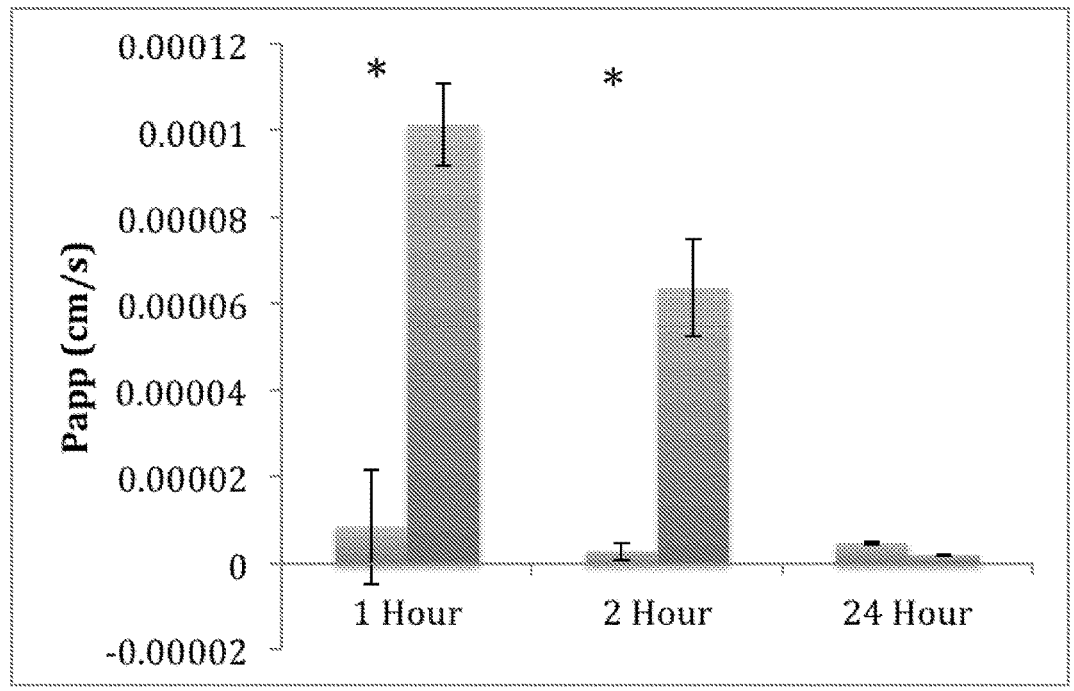
FIG. 13 shows the transcellular permeation of LPV loaded nanoemulsions as compared to the transcellular permeation of an aqueous solution of LPV.
Figure 13B:
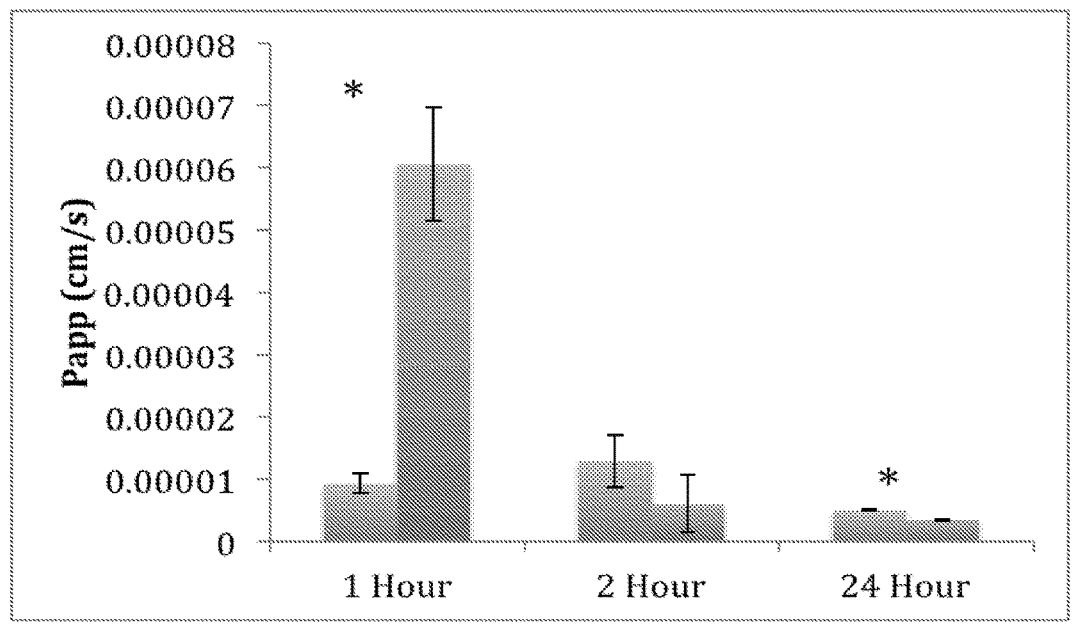
Figure 14A:
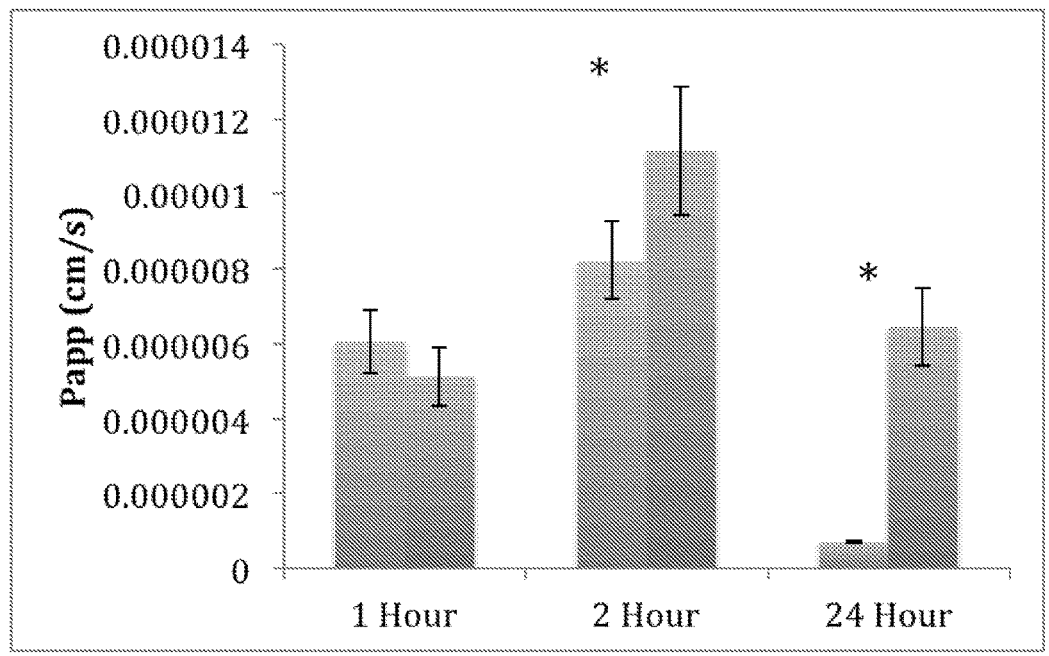
FIG. 14 shows the transcellular permeation of EFV loaded nanoemulsions as compared to the transcellular permeation of an aqueous solution of EFV.
Figure 14B:
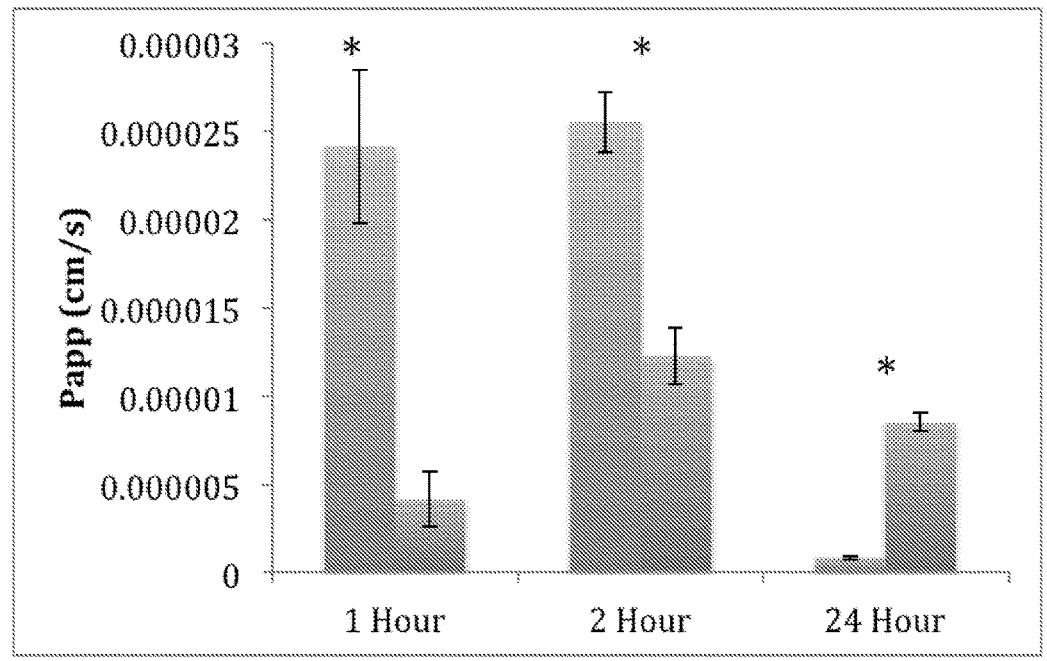

FIG. 13 shows the transcellular permeation of LPV loaded nanoemulsions (right hand bars) as compared to the transcellular permeation of an aqueous solution of LPV (left hand bars), in the Apical to Basolateral direction (blood to gut) (A) and the Basolateral to Apical direction (gut to blood) (B). Stars indicate statistical significance between the data sets FIG. 14 shows the transcellular permeation of EFV loaded nanoemulsions (right hand bars) as compared to the transcellular permeation of an aqueous solution of EFV (left hand bars), in the Apical to Basolateral direction (blood to gut) (A) and the Basolateral to Apical direction (gut to blood) (B). Stars indicate statistical significance between the data sets Transcellular Permeation Assay Caco-2 cells were seeded at a density of 35,000 cells per well in the apical chamber of a 24 well Corning® HTS® transwell plate, and left to adhere for 24 hours. After this time, culture media was replenished by removal with an aspirator, also removing those cells that had not adhered. Culture media used was DMEM supplemented with 15% fetal bovine serum, which was continually replenished every other day for a three-week period. After three weeks had passed, the formation of an intact caco-2 monolayer was assessed using a trans-epithelial electrical resistance (TEER) probe, resistance values in excess of 600 ohms indicated that the assay was ready to use, due to the cells forming tight monolayers between the wells, thus causing the electrical resistance to increase.

During the assay, culture media was removed from wells and replaced with 15% FBS supplemented DMEM that had a final concentration of 10 µM aqueous solution or nanoemulsion equivalent of LPV or EFV. In different wells the apical or basolateral chambers (donor chambers) were loaded with drug or nanoemulsion containing media, with the opposite chambers (acceptor chambers) of those wells being filled with fresh drug-free media. Samples were taken from both apical and basolateral chambers from all wells at 1, 2, and 24 hour time periods. Samples were then immediately frozen at −40° C. for subsequent batch analysis via high performance liquid chromatography to determine the concentration of the drug in the sample.

The apparent permeability (Papp) was calculated using the following equation:

$$Papp=((A/T)*(V))/(S*0.3).$$

Where A is the concentration in the sample, T is the time in seconds at which the sample was collected, V is the total volume of sample contained in the chamber being sampled, S is the initial starting concentration of the drug and 0.3 is the surface area in $cm^2$ of the transwell insert on which the Caco-2 cells are grown.

Transcellular Permeation of LPV Loaded Nanoemulsions

There was a statistically significant (as determined by independent samples t-test using SPSS software) greater permeation seen for the nanoemulsion formulation of LPV at both 1 hour and 2 hour time points, with Papp values of $1 \times 10^{-4}$ vs $8.4 \times 10^{-6}$ (p=<0.05) at 1 hour and $6.4 \times 10^{-5}$ vs $2.7 \times 10^{-6}$ (p=<0.05) at 2 hours. After 24 hours there was no difference seen between the aqueous and nanoemulsion systems.

The Papp data for aqueous and nanoemulsion LPV initially showed that the apical to basolateral permeation was improved for the nanoemulsion (Papp values of $1 \times 10^{-4}$ vs $8.4 \times 10^{-6}$ (p=<0.05)) at the 1-hour time point. However it is also observed that the permeation in the opposite direction, that is basolateral to apical, is also much higher than the aqueous value (Papp value of $6.1 \times 10^{-5}$ compared with $9.3 \times 10^{-6}$). LPV is a known p-gp (a drug transporting protein found on the surface of some cells) substrate, which would make it likely to undergo efflux back out of the Caco-2 cells in the B-A direction (simulating movement from the systemic circulation where the drug is needed, back into the intestinal system). However, the conditions of the transwell assay system do not ideally match those that would be found in an animal model or indeed the human body, as the drug would not accumulate and build up in the basolateral compartment, instead being carried away by the systemic circulation (Caco-2 transwells are static assays). Additionally caco-2 cells do not form as tight monolayers as those found in vivo, which has been cited as a source for the underestimation of compounds that permeate via paracellular routes (i.e. between the cells, rather than through them), as opposed to transport (movement into the cells and then out the other side). For this reason it is very promising that the large increase in permeation in the A-B direction at 1 hour would likely result in more drug crossing the intestinal barrier in an in vivo system.

The data for the 2 hour time point again showed there was an increase in the permeation from apical to basolateral for the nanoemulsion compared to the aqueous solution of LPV ($6.4 \times 1^{-5}$ vs $2.7 \times 10^{-6}$ (p=<0.05)). However, in this instance the same increase in the basolateral to apical direction was not observed ($6.0 \times 10^{-6}$ vs $1.3 \times 10^{-5}$ (p=0.11)), suggestive that the permeation of LPV nanoemulsions is superior to LPV aqueous solution.

The difference in permeation between the aqueous and nanoemulsion formulations could suggest that the drug is being transported across the monolayer by different mechanisms. As the nanoemulsion would be unlikely to be transported across the monolayer via transport proteins, it would imply that the nanoemulsion droplets permeate across the monolayer via paracellular transport, which has been seen in previous studies of nanoparticle permeation. This could also explain why there is such a large increase in B-A permeation of the nanoemulsion over the aqueous, as the formulation allows for the movement of drug between the small gaps in the monolayer as it is entrapped within the emulsion droplet. A possible explanation for the reduction in B-A permeation at 2 hours as compared with at 1 hour for the nanoemulsion could be that the nanoemulsions have begun to aggregate and can no longer pass through the monolayer via paracellular means.

Transcellular Permeation of EFV Loaded Nanoemulsions

After 1 hour there was no increase observed in the apparent permeability between the nanoemulsion formulation and aqueous EFV solution. However after both 2 and 24 hours, the EFV nanoemulsion had significantly increased permeability ($8.2 \times 10^{-6}$ for aqueous solution compared to $1.1 \times 10^{-5}$ for EFV nanoemulsion at 2 hours (p=<0.05)) and ($7.0 \times 10^{-7}$ for aqueous solution compared with $6.4 \times 10^{-6}$ for EFV nanoemulsion at 24 hours (p=<0.05)).

At 1 and 2 hours the B-A permeability of EFV aqueous solution was increased compared to EFV nanoemulsion, but again it should be noted that in a static system like the transwell assay, B-A permeability is a less useful measure than A-B. It is still promising to see a reduction in B-A permeability. Another issue of the Caco-2 transwell system is that Caco-2 cells do not express cytochrome P450 2B6, and as this is the main route of metabolism for EFV, there will be an underestimation as to the protective effects that having the drug within the emulsion droplet could have, if it is protected from metabolism. It should also be noted that EFV already shows good intestinal permeability, as it has class 2 status with the FDA (poor solubility, high intestinal permeability), so to have seen further improvements suggests the nanoemulsion formulation has inherently good permeability characteristics.

Furthermore the nanoemulsion formulation could be directly diluted into aqueous culture media and used in the assay, without need for prior dissolution into a solvent (as is necessary to make up the aqueous solutions of LPV and EFV). This could be highly attractive for making more tolerable and safe oral formulations that are easily dose adjustable, especially as in a pediatric setting where the use of solvents such as ethanol is a concern.

The invention claimed is:

1. An oil-in-water emulsion comprising:
  i. a drug or prodrug, and
  ii. a non-gelled branched polymer emulsifier, wherein said non-gelled branched polymer is a branched vinyl polymer, wherein the ends of at least some of the chains of said branched vinyl polymer terminate in an alkyl chain of 5 carbon atoms or more, and wherein the oil-in-water emulsion takes the form of particles having a z-average diameter of no greater than about 1000 nm.

2. The oil-in-water emulsion as claimed in claim 1 wherein said alkyl chain is of 10 carbon atoms or more.

3. The oil-in-water emulsion as claimed in claim 1 wherein said alkyl chain is saturated and unsubstituted.

4. The oil-in-water emulsion as claimed in claim 1 wherein said alkyl chain is an initiator residue.

5. The oil-in-water emulsion as claimed in claim 4 wherein said branched vinyl polymer comprises PEG moieties.

6. The oil-in-water emulsion as claimed in claim 4 wherein said branched vinyl polymer is branched by virtue of EGDMA monomer.

7. The oil-in-water emulsion as claimed in claim 1 wherein not all polymer chains carry said alkyl chain of 5 carbon atoms or more.

8. The oil-in-water emulsion as claimed in claim 1 wherein 50% or fewer of the polymer chains carry said alkyl chain of 5 carbon atoms or more.

9. A pharmaceutical composition, optionally for oral administration, comprising an oil-in-water emulsion as claimed in claim 1.

10. A method of treating a patient in need of anticoagulant therapy, said method comprising administering to said patient an effective amount of an oil-in-water emulsion as claimed in claim 1.

11. In a method of medical treatment characterized by administering an effective amount of a pharmaceutical composition to a subject in need thereof, wherein the improvement comprises administering a pharmaceutical composition as claimed in claim 9.

12. An emulsifier as defined in claim 1.

13. A method of preparing an oil-in-water emulsion as defined in claim 1, comprising mixing an oil phase with an aqueous phase in the presence of an emulsifier, wherein said emulsifier is a non-gelled branched vinyl polymer, wherein the ends of at least some of the chains of said branched vinyl polymer terminate in an alkyl chain of 5 carbon atoms or more, and wherein the oil-in-water emulsion takes the form of particles having a z-average diameter of no greater than about 1000 nm.

14. The method as claimed in claim 13 wherein said oil phase further comprises a solvent which is miscible with the oil, said solvent being allowed to evaporate to produce the final emulsion.

15. The method as claimed in claim 13 wherein said branched vinyl polymer is prepared using an initiator which has an alkyl chain of 5 carbon atoms or more, and an initiator which does not.

16. The pharmaceutical composition as claimed in claim 9, wherein said composition is formulated for oral administration.

17. The oil-in-water emulsion as claimed in claim 5, wherein said branched vinyl polymer comprises PEG moieties from an oligo(ethylene glycol) methacrylate (OEGMA) monomer.

18. The method as claimed in claim 10, wherein said emulsion is administered to said patient orally.

19. The method as claimed in claim 11, wherein said composition is formulated for oral administration and is administered orally to said subject.

* * * * *